United States Patent [19]

Higashi et al.

[11] Patent Number: 6,027,710

[45] Date of Patent: *Feb. 22, 2000

[54] RADIATION-PROTECTING AGENT

[75] Inventors: Kazuo Higashi, Sodegaura; Komei Washino, Ichihara, both of Japan

[73] Assignee: Nihon Medi-Physiscs Co., Ltd., Hyogo-ken, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/923,002

[22] Filed: Sep. 16, 1997

[30] Foreign Application Priority Data

Sep. 18, 1996 [JP] Japan .................................. 8-267929

[51] Int. Cl.⁷ .......................... A61K 51/00; A61M 36/14
[52] U.S. Cl. ................... 424/1.65; 424/1.11; 424/1.73; 424/1.81; 424/1.85; 424/1.89; 534/11
[58] Field of Search .................... 424/1.11, 1.37, 424/1.49, 1.65, 1.73, 1.81, 1.85, 1.89, 9.1, 9.3, 9.4, 9.5, 9.6, 1.77; 534/7, 10–16; 552/106, 107, 113, 115; 252/400.62, 404; 423/584; 430/393, 430, 461; 514/11, 970; 546/342; 562/478; 987/55

[56] References Cited

U.S. PATENT DOCUMENTS

| | | | |
|---|---|---|---|
| 4,364,920 | 12/1982 | Winchell | 424/1 |
| 4,489,053 | 12/1984 | Azuma et al. | 424/1 |
| 4,645,660 | 2/1987 | Takahashi et al. | |
| 4,857,299 | 8/1989 | Chia et al. | |
| 4,880,615 | 11/1989 | Charleson | 424/1.11 |
| 5,219,556 | 6/1993 | Wolfangel | 424/1.11 |
| 5,384,113 | 1/1995 | Deutsch et al. | 424/1.69 |
| 5,393,512 | 2/1995 | Vanderheyden et al. | 424/1.53 |

FOREIGN PATENT DOCUMENTS

| | | |
|---|---|---|
| 0 123 314 A2 | 10/1984 | European Pat. Off. |
| 0 313 712 A1 | 3/1989 | European Pat. Off. |
| 0 508 724 A1 | 10/1992 | European Pat. Off. |
| 57-36894 | 8/1982 | Japan ............ A61K 47/00 |
| 2-33019 | 7/1990 | Japan ............ A61K 49/02 |
| 57-6409 | 2/1997 | Japan ............ A61K 49/02 |
| 1 541 070 | 4/1976 | United Kingdom ....... G21G 4/04 |
| 93/02652 | 2/1993 | WIPO . |

*Primary Examiner*—Jose' G. Dees
*Assistant Examiner*—Dameron Jones
*Attorney, Agent, or Firm*—Sughrue, Mion, Zinn, Macpeak & Seas, PLLC

[57] ABSTRACT

The present invention provides a radiation-protecting agent which protects the active ingredient of radiopharmaceuticals against the radiolysis caused by a reaction of the active ingredient with water radicals formed by radiolysis of water, without decomposing the reactive active ingredient such as readily reducible active ingredient. The radiation-protecting agent of the present invention is characterized by comprising an organic compound usable in medical drugs and having high physiological acceptability and protecting the radiolabeled active ingredient of radiopharmaceuticals against the action of radiation. The reaction rate constant of said organic compound with OH radical, H radical or hydrated electron must be in the range of from $1\times10^8$ to $5\times10^{10}$ $M^{-1}s^{-1}$, and when added to radiopharmaceuticals, molar concentration of the organic compound must be at least 50 times as high as molar concentration of the active ingredient.

9 Claims, 4 Drawing Sheets

○ Air-saturated (Wavelength:368nm)
△ Argon-saturated (Wavelength:368nm)
● Air-saturated (Wavelength:461nm)
▲ Argon-saturated (Wavelength:461nm)

*Wavelength: 368nm

RADIATION-PROTECTING AGENT

BACKGROUND OF THE INVENTION

1. Field of the Invention

The present invention relates to radiation-protecting agents which protect the active ingredient of radiopharmaceuticals against radiolysis.

2. Related Art Statement

Radiopharmaceuticals are drugs to be administered into a living body for the purpose of nuclear medicine diagnosis or radiotherapy. In general, radiopharmaceuticals comprise a radioisotope ion itself or an organic compound stably bound with a radioisotope as an active ingredient, and further contain pharmaceutically necessary additives, and many of the radiopharmaceuticals are formulated as aqueous solution. When an organic compound is used as an active ingredient, the radioisotope is incorporated into the molecular structure of active ingredient through covalent bond or coordination bond.

In radiopharmaceuticals, the radiation emitted from radioisotope decomposes the active ingredient by direct action or indirect action of radiation. The term "direct action" means decomposition caused by the direct collision of the radiation itself emitted from radioisotope against active ingredient molecule, while the term "indirect action" means decomposition of active ingredient molecule caused by the attack of water radicals such as OH radical, H radical and hydrated electron which are formed when the energy of the radiation emitted from radioisotope is absorbed by water molecule constituting the solvent. These actions of radiation are called radiolysis, and the radiolysis of an active ingredient is almost exclusively caused by the indirect action, in case of aqueous radiopharmaceuticals in which the concentration of active ingredient is generally low. The number of radicals generated per 100 eV of absorbed radiation energy is called radical yield, which is 2.5 for OH radical, 0.5 for H radical, and 2.7 for hydrated electron. These values and the characteristic feature of the radical reaction suggest that the predominant water radical participating in radiolysis is OH radical in most cases.

Further, water radicals form hydrogen peroxide in the process of the recombination reaction thereof. The hydrogen peroxide thus formed disturbs the active ingredient-forming reaction (complex formation) when technetium-99m (hereinafter abbreviated to Tc-99m), a typical radionuclide for radiopharmaceuticals, is linked to active ingredient through coordination bond. In addition, the hydrogen peroxide accelerates elimination of Tc-99m from active ingredient. In radiopharmaceuticals containing Tc-99m, a reductant (usually, a stannous salt) is added for the purpose of reducing pertechnetate (hereinafter abbreviated to $^{99m}TcO_4^-$) and forming a complex with a chelating agent. Hydrogen peroxide oxidizes this reductant to disturb the complex-formation or re-oxidizes the coordinated Tc-99m to accelerate the elimination of Tc-99m. Since the above-mentioned attack of water radicals and the oxidative action of hydrogen peroxide cause decomposition of active ingredient and thereby markedly deteriorate the quality of radiopharmaceuticals, it has hitherto been conventional to add a stabilizer to radiopharmaceuticals in order to prevent the deterioration of drug quality.

In Japanese Patent Publication JP-B-82036894, JP-B-82006409 and JP-B-90033019, there is disclosed a technique of adding ascorbic acid or erythorbic acid as a stabilizer for radiopharmaceuticals labeled with Tc-99m, one of the representative radionuclide used in radiopharmaceuticals.

Ascorbic acid and erythorbic acid proposed as stabilizer in these patent gazettes have a general characteristic feature that they are both reductive substances, and their amount to be added is prescribed based on the amount of stannous salt which is a reductant for Tc-99m. The nature of their stabilizing action lies in decomposing hydrogen peroxide due to the reductivity of these stabilizers and thereby preventing the oxidation of the stannous salt used as reductant. However, these stabilizers, namely ascorbic acid and erythorbic acid, are unusable at all when a readily reducible active ingredient or additive is present in the drug formulation because these stabilizers reductively decompose such active ingredient or additive. For example, in a radiopharmaceutical comprising an active ingredient having porphyrin rings as fundamental chemical structure, the active ingredient is decomposed through a reaction with ascorbic acid as mentioned below, and thereby loses the original pharmaceutical activity.

SUMMARY OF THE INVENTION

In view of the above-mentioned situation, the objective of the present invention consists in providing radiation-protecting agents for use in radiopharmaceuticals which prevents an active ingredient from decomposition caused by the reaction between active ingredient and water radicals formed by radiolysis of water, without reductively decomposing the readily reducible active ingredient.

The present invention provides a radiation-protecting agent comprising an organic compound having high physiological acceptability and, when added to a radiopharmaceutical, protecting the radiolabeled active ingredient of the drugs against the action of radiation. Said organic compound preferably has a high reaction ate constant with OH radical, H radical and hydrated electron, and the reaction rate constant is particularly in the range of from $1 \times 10^8$ to $5 \times 10^{10}$ $M^{-1}s^{-1}$. When the radiation-protecting agent of the present invention is to be added to radiodiagnostic agents or radiotherapeutic drugs, molar concentration of the radiation-protecting agent is usually 50 times or more as high as the molar concentration of the active ingredient.

DETAILED DESCRIPTION OF THE INVENTION

As used in the present invention, the term "organic compound having high physiological acceptability" means an organic compound exhibiting neither toxicity nor pharmacological action at the clinical dose when added to a radiopharmaceutical as an additive. Examples of such organic compound having high physiological acceptability include monosaccharides, disaccharides, organic acids, salts thereof and esters thereof.

The active ingredient of the radiopharmaceuticals in the present invention comprises an organic compound capable of forming a stable linkage or a stable complex with a radioisotope ion or a radioisotope, and is used for medical diagnosis or therapy. Examples of the active ingredient of radiopharmaceuticals for diagnosis include technetium ($^{99m}$Tc) hydroxymethylenediphosphonate, technetium ($^{99m}$Tc) dimercaptosuccinate, N-pyridoxyl-5-methyltryptophane technetium ($^{99m}$Tc), indium ($^{111}$In) diethylenetriaminepentaacetate, N-isopropyl-p-iodoamphetamine ($^{123}$I), 15-(p-iodophenyl)-3(R,S)-methylpentadecanoic acid ($^{123}$I), 7-[1-(2-hydroxyethyloxy)ethyl]-12-ethenyl-3,8,13,17-tetramethylporphine-2,18-dipropanoic acid manganese (III) complex diethylenetriaminepentaacetic acid monoester technetium ($^{99m}$Tc), and the like. Examples of the active ingredient of radiotherapeutic drug include samarium ($^{153}$Sm) ethylenediaminetetra-methylenephosphonate, tin ($^{117m}$Sn) diethylenetriamine-pentaacetate, rhenium ($^{186}$Re) hydroxyethylidenediphosphonate, and the like.

The radiation-protecting agent of the present invention must capture most of the water radicals in competition with the active ingredient and water radicals. For this reason, the radiation-protecting agent must be selected from compounds having greater radical reaction rate constant than that of the active ingredient, or molar concentration of the radiation-protecting agent must be overwhelmingly higher than that of the active ingredient. In many cases, however, it is not always possible to add the additive in a large quantity, because of restriction in individual drug formulation, such as obstruction of labeling reaction by the presence of excess amount of additive. Accordingly, the radiation-protecting agent must have a high reaction rate constant with water radicals, namely OH radical, H radical and hydrated electron. In other words, the reaction rate constant between the radiation-protecting agent and water radicals must be higher than the so far known reaction rate constants between water radicals and common low molecular weight substances which are usually in the range of from $10^6$ to $10^9$ M$^{-1}$s$^{-1}$. It is preferably necessary that the reaction rate constant between the radiation-protecting agent and water radicals is in the range of from $1\times10^8$ to $5\times10^{10}$ M$^{-1}$s$^{-1}$, in order to exhibit a reliable effect as a radiation-protecting agent.

Examples of the radiation-protecting agent of the present invention include monosaccharides such as glucose, fructose, mannose, galactose, arabinose and sorbitol; disaccharides such as sucrose, maltose and lactose; and organic acids such as sialic acid, lactic acid, benzoic acid and the like.

The radiation-protecting agent of the present invention is reactive with the water radicals formed by radiolysis of water as has been mentioned above, however, it is equally important that the agent should be unreactive with the active ingredient of radiopharmaceutical. Based on this idea, the present inventors selected a compound containing porphyrin ring as a highly reactive active ingredient, and its reactivity with the radiation-protecting agent of the present invention was investigated. The compound selected herein could form a stable complex with radioisotope and was expected to be useful as an active ingredient of radiopharmaceutical used as a diagnostic or therapeutic agent, and at the same time the compound was highly reactive in reactions such as oxidation-reduction reaction, and the change of its state could readily be detected by spectral measurement after the reaction.

In order to know whether or not the candidate radiation-protecting compounds selected above could actually protect an active ingredient of radiopharmaceutical from the indirect action of radiation, the reaction rate constant between the candidate compound and OH radical (hereinafter abbreviated to OH.), one of the water radicals, was determined in a bimolecular competitive reaction system. Since water radicals include the above-mentioned three species and the three species are usually comparable to one another in the reaction rate constant, OH. was selected in this experiment due to its highest radiolytic activity. In the measurement, a sample substance of unknown rate constant was added in various concentration to a solution of a standard substance of known rate constant with OH., and the sample substance and the standard substance were made to react with OH. competitively. The quantity of the standard substance having reacted with OH. and thereby having been decomposed was determined from the change in UV absorption spectrum thereof, based on which the reaction rate constant of the sample substance was calculated. (Henglein et al., translated by Junkichi Soma et al., Fundamental Radiation Chemistry, published by Tokyo Kagaku Dojin) Details of the theory are mentioned below.

In the field of radiation chemistry, p-nitrosodimethylaniline (hereinafter abbreviated to NDA) is used as a standard OH. scavenger for measurement of reaction rate constant. When NDA reacts with OH., it decomposes to lose the light absorption peak at 440 nm. G value (a numerical value indicating the magnitude of various events taking place upon irradiation with radiation; the number of molecules of a substance undergoing a change at the time when the substance has absorbed 100 eV of radiation energy) of this reaction is 1.2, and its reaction rate constant is $1.25\times10^{10}$ M$^{-1}$s$^{-1}$. When a sample substance X reacts with OH. in competition with standard substance NDA and the secondary reaction between X radical and NDA is negligible, the reaction rate constant between X and OH. can be determined from the reaction rate constant between the standard substance and OH., according to the reaction rate theory in homogeneous system. $^{99m}$TcO$_4^-$ is not regarded as a reaction element, because its concentration is extremely low. In order to simplify the reaction system, the solution is replaced with N$_2$O, and hydrated electron ($e_{aq}^-$) is converted to OH.:

[N$_2$O]=ca. 24 mM (saturated with N$_2$O)

In a system in which only X and NDA exist, OH. disappears through the following reaction:

(NDA*: reaction product)

(X*: reaction product)

The disappearance velocity of OH· is expressed by the following Formulas 1 and 2:

$$-d[OH\cdot]_{NDA}/dt = k_1[NDA][OH\cdot]$$ Formula 1 wherein $k_1$ is reaction rate constant between OH· and NDA;

$$-d[OH\cdot]_X/dt = k_X[X][OH\cdot]$$ Formula 2 wherein $k_X$ is reaction rate constant between OH· and X.

The total disappearance velocity of OH· is the sum of Formulas 1 and 2, and expressed by the following Formula 3:

$$-d[OH\cdot]/dt = (-d[OH\cdot]_{NDA}/dt) + (-d[OH\cdot]_X/dt)$$ Formula 3

The fraction of OH· reacting with NDA, namely $F_{NDA}$, is expressed by Formula 4, and reciprocal of Formula 4 is Formula 5:

$$F_{NDA} = (-d[OH\cdot]_{NDA}/dt)/(-d[OH\cdot]/dt) = k_1[NDA][OH\cdot]/(k_1[NDA][OH\cdot] + k_X[X][OH\cdot])$$ Formula 4

$$1/F_{NDA} = 1 + k_X[X]/k_1[NDA]$$ Formula 5

Formula 5 indicates that $1/F_{NDA}$ is a first order function with regard to [X]. Conversion of Formula 5 gives Formula 6:

$$1/F_{NDA} = 1 + k_X \cdot C \cdot [X]$$ Formula 6 wherein $C = 1/k_1[NDA]$, $k_1$ is $1.25 \times 10^{10}$ M$^{-1}$s$^{-1}$, and [NDA] indicates an experimentally determined constant concentration.

In Formula 6, $k_X$ can be determined by plotting $1/F_{NDA}$ against various [X] and measuring the slope.

$1/F_{NDA}$ can be determined in the following manner. NDA shows an intense absorption at 440 nm in aqueous solution, while its reaction product with OH·, namely NDA*, shows no absorption at 440 nm. In an aqueous solution, the decrease of absorption at 440 nm observed in the absense of X indicates total quantity of OH· formed. In an aqueous solution of NDA containing X, the decrease of NDA absorption becomes smaller in proportion to progress of the reaction between X and OH·. If the decrease of light absorption in the absence of X is expressed by $\Delta Abs_0$ and the decrease of light absorption in the presence of X is expressed by $\Delta Abs_X$, the fraction of OH· having reacted with NDA is expressed by Formula 7. By inserting Formula 7 into Formula 5, Formula 8 is obtained:

$$F_{NDA} = \Delta Abs_X / \Delta Abs_0$$ Formula 7

$$\Delta Abs_0 / \Delta Abs_X = 1 + k_X[X]/k_1[NDA]$$ Formula 8

By optimizing the concentration of NDA and the quantity of $^{99m}$Tc in a region making easy the measurement of $\Delta Abs$ change in this reaction system and plotting the experimental data according to Formula 8, slope $k_X$ can be determined by the least square method. Experiments based on the above-mentioned theory revealed that candidate compounds belonging to monosaccharide, disaccharide and organic acid all have a sufficiently high reaction rate constant and therefore radiation-protecting effect can be expected therefrom.

Subsequently, a saccharide or an organic acid having safety and physiological acceptability enough for use as a drug additive was blended with an active ingredient, and examined for radiation-protecting effect under an expected handling condition where the composition is put to practical use as radiopharmaceutical. As a result, glucose, fructose, sucrose, sorbitol, meglumine, lactic acid, benzoic acid, etc. exhibited a high radiation-protecting effect. Details are mentioned later in Examples.

The purpose of the addition of a radiation-protecting agent to radiopharmaceutical consists in protecting the active ingredient molecule against the indirect action of radiation. The mechanism of indirect action of radiation is considered to be similar regardless of the kind of radiation, namely α-ray, β-ray or γ-ray, and thus regardless of the kind of isotopes. Accordingly, the radiation-protecting agent of the present invention and the use thereof are effective for all kind of radioisotopes used in radiopharmaceuticals. The radioisotopes generally used in radiopharmaceuticals are Tc-99m, I-123, I-131, Ga-67, In-111, Ru-97, Pb-203, C-11, N-13, O-15, F-18, Cu-62, Rb-87, Y-90, I-131, Sm-153, Dy-165, Ho-166, Lu-177, Re-186, Re-188, At-211, Cu-67, etc.

The radiation-protecting agents of the present invention may be added to compositions for use in preparing radiopharmaceuticals either previously or afterwards. The form of the said composition may be any of freeze-dried composition, simple powder mixture, water-soluble liquid and freeze-dried product thereof. Further, a pH regulator such as an acid or a base, an isotonizing agent such as sodium chloride, a preserver such as benzyl alcohol, or a freeze-dry excipient such as lactose may be added to the composition, and addition of such additives makes no trouble on the practice of the present invention.

When added to radiopharmaceuticals, the radiation-protecting agent of the present invention competitively protects the active ingredient against the attack of water radicals formed by radiolysis of water, and thereby prevents radiopharmaceuticals from deterioration of quality. This protecting effect can be expected when the reaction rate constant between the radiation-protecting agent and water radicals is in the range of from $1 \times 10^8$ M$^{-1}$s$^{-1}$ to $5 \times 10^{10}$ M$^{-1}$s$^{-1}$ and a chemical inertness of the radiation-protecting agent to active ingredient, namely unreactivity thereof, is secured.

PREFERRED EMBODIMENTS OF THE INVENTION

EXAMPLE 1

In order to ascertain that porphyrin derivative is suitable model compound for searching and studying radiation-protecting agents, the radiolysis of 7-[1-(2-hydroxyethyloxy)ethyl]-12-ethenyl-3,8,13,17-tetramethyl-porphine-2,18-dipropanoic acid manganese (III) complex diethylenetriaminepentaacetic acid monoester (HP-DTPA) which is one of the porphyrin derivatives was studied.

A solution of $^{99m}$TcO$_4^-$ in an amount of 10–50 mCi as expressed in terms of quantity of radioactivity was added to a solution of HP-DTPA (0.25 or 0.20 mg/ml, solvent: purified water, pH 5). After tightly sealing the resulting mixture in a glass vial, the mixture was left to stand under either air-saturated or argon-saturated condition at room temperature for 24 hours. Then, UV absorption spectrum and fluorescence spectrum of the solution were measured. The changes in UV absorption spectrum and fluorescence spectrum were measured using a control sample containing no $^{99m}$TcO$_4^-$.

Figure 1:
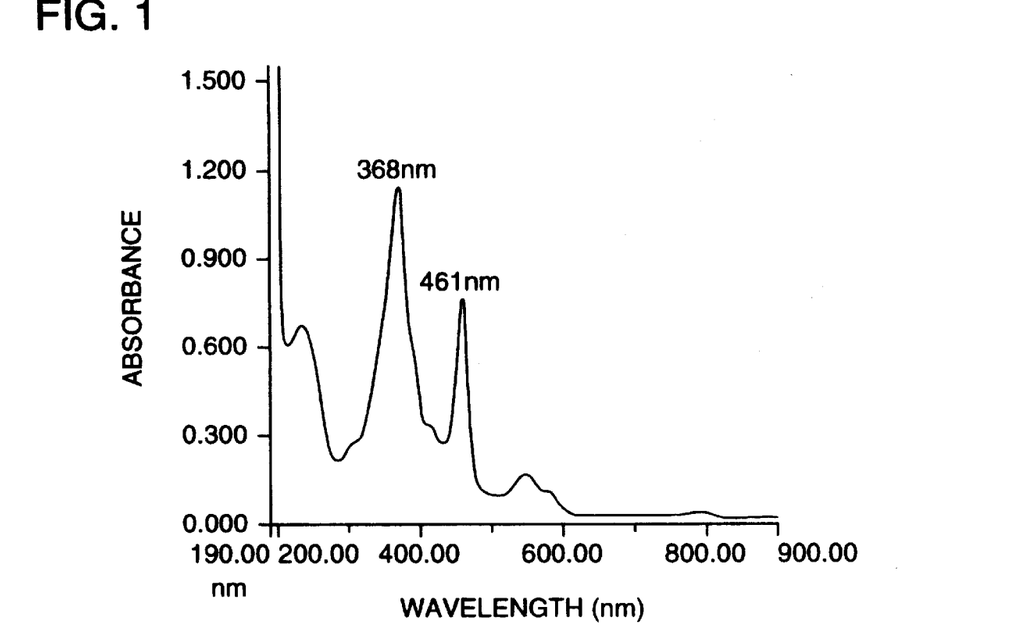
FIG. 1 is the UV absorption spectrum of a solution of diethylenetriaminepentaacetic acid monoester of 7-[1-(2-hydroxyethyloxy)ethyl]-12-ethenyl-3,8,13,17-tetramethyl-porphine-2,18-dipropanoic acid manganese (III) complex (hereinafter abbreviated to HP-DTPA).
Figure 2:
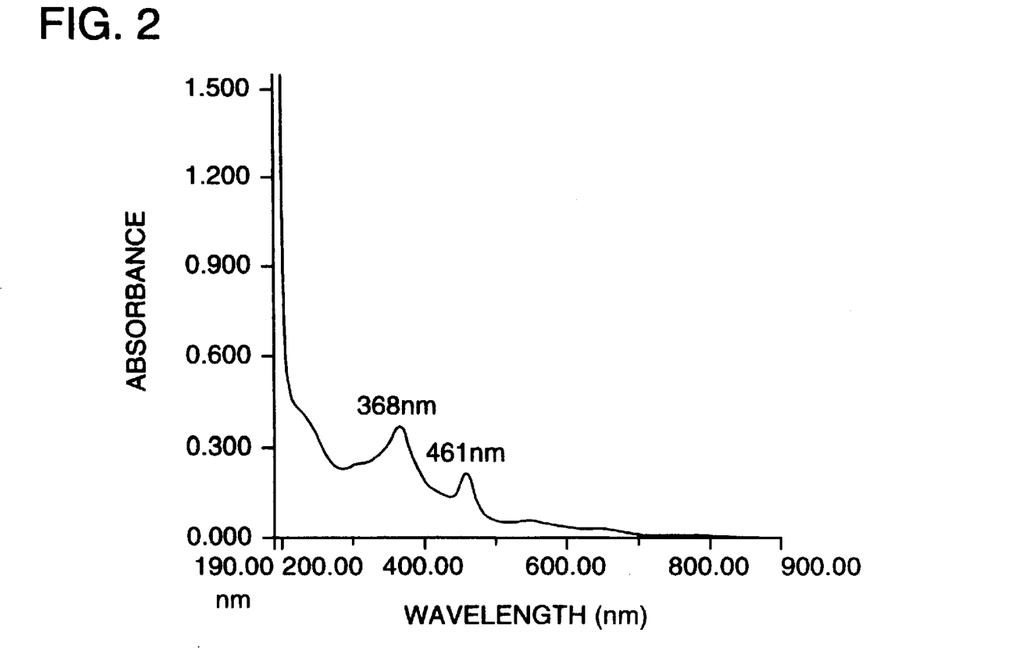
FIG. 2 is the typical UV absorption spectrum of a solution of HP-DTPA which was allowed to be radiolyzed in an air-saturated solution at room temperature for 24 hours.
Figure 3:
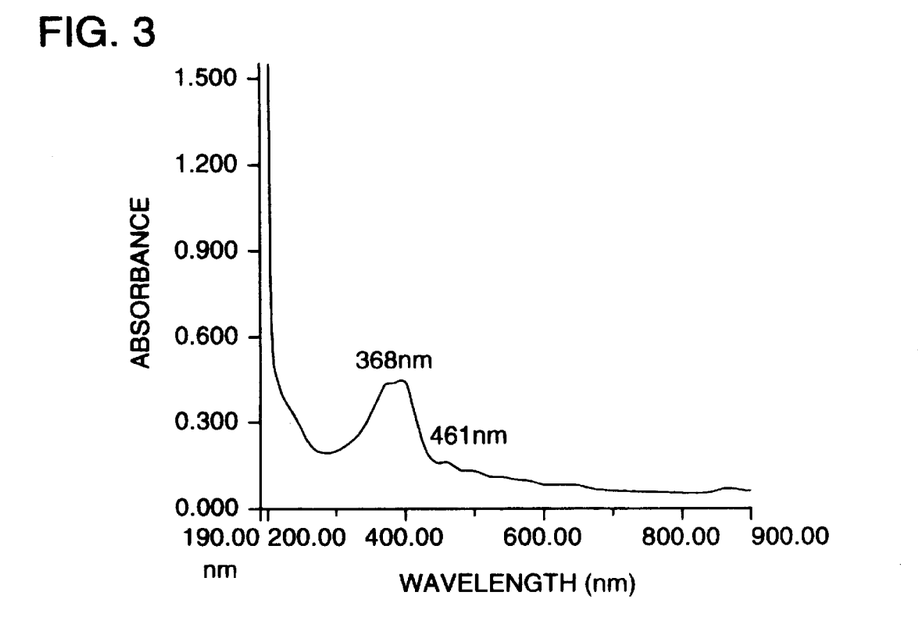
FIG. 3 is the typical UV absorption spectrum of a solution of HP-DTPA which was allowed to be radiolyzed in an argon-saturated solution at room temperature for 24 hours.
Figure 4:
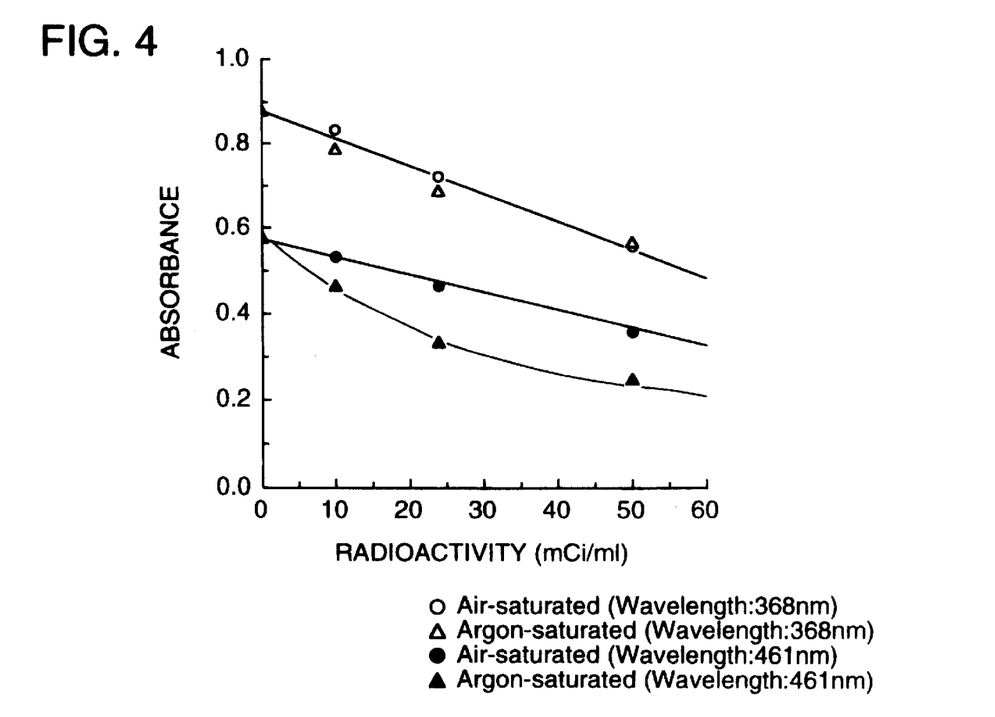
FIG. 4 is a graph given by plotting the decrease of UV absorption peaks at 368 nm and 461 nm of HP-DTPA brought about by radiolysis, against the quantity of radioactivity (Tc-99m) added.
Figure 5:
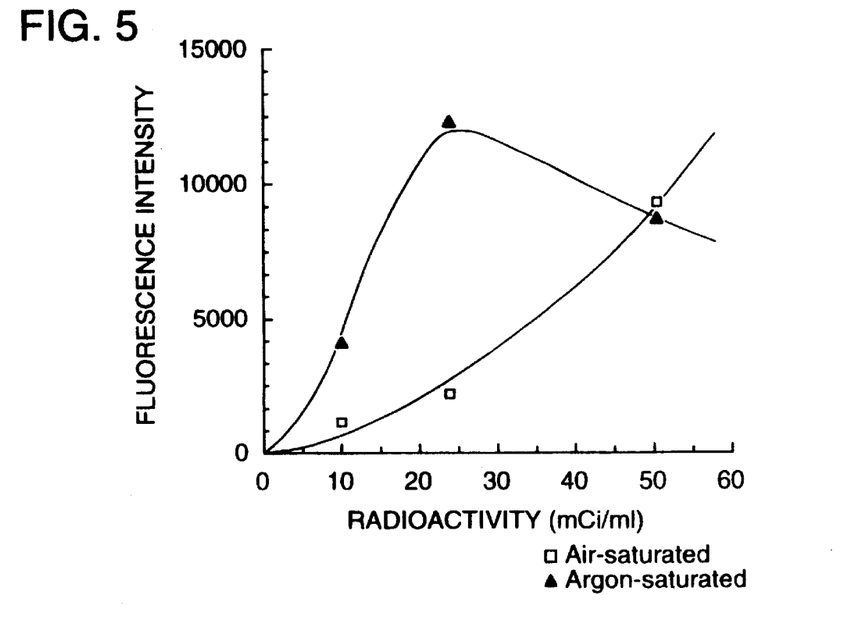
FIG. 5 is a graph given by plotting the fluorescence intensity of the radiation-decomposed product of HP-DTPA against the quantity of radioactivity (Tc-99m) added.

FIG. 1 illustrates UV absorption spectrum of the control sample, HP-DTPA solution containing no $^{99m}$TcO$_4^-$. FIG. 2 and FIG. 3 illustrate UV absorption spectra of samples prepared by adding 50 mCi of $^{99m}TcO_4^-$ solution to control HP-DTPA solution, and allowing the resulting mixture to stand under either air-saturated condition (FIG. 2) or argon-saturated condition (FIG. 3) for 24 hours at room temperature. It was shown from these results that the UV absorption peaks at 368 nm and 461 nm, characteristic of porphyrin derivatives, have been diminished by radiolysis. FIG. 4 is a graph obtained by plotting the decrease of UV absorption peak against radioactivity mixed in the range of 10–50 mCi in samples allowed to stand for 24 hours under the same condition as above. Absorbance at 368 nm has decreased in proportion to the quantity of radioactivity added. At the same time, the addition of radioactivity produced a fluorescent substance, with fluorescence intensity also in proportion to the quantity of radioactivity added (FIG. 5). The above-mentioned change was not observed when a $^{99m}TcO_4^-$-free HP-DTPA solution was allowed to stand at room temperature, nor when an cooled-down $^{99m}TcO_4^-$ solution was added. An HPLC analysis of the HP-DTPA solution mixed with $^{99m}TcO_4^-$ has detected some peaks assignable to decomposed products by radiolysis. The above-mentioned experiments have proved that porphyrin derivatives are quite active to radiolysis. As mentioned below, the reaction rate constant of HP-DTPA with OH. is as great as $2.8 \times 10^{10}$ $M^{-1}s^{-1}$.

EXAMPLE 2

The radiation-protecting agent of the present invention cannot be effective, unless the reaction rate constant thereof with water radicals is sufficiently high. In this experiment, the reaction rate constant between a radiation-protecting agent and OH. having the highest reactivity among water radicals was measured. The samples of radiation-protecting agent, namely compounds X, subjected to measurement in this example were saccharides (glucose and fructose), amino acid (glycine) an organic acids (lactic acid and benzoic acid). All these compounds had already been proved their safety and physiological acceptability as drug additives.

A solution of X having a varied concentration (0, $2 \times 10^{-5}$, $5 \times 10^{-5}$, $1 \times 10^{-4}$, $2 \times 10^{-4}$ and $5 \times 10^{-4}$ M) and a solution of $^{99m}TcO_4^-$ (20 mCi/ml) were added to a diluted solution of NDA ($2 \times 10^{-5}$ M). After allowing the mixtures thus obtained to stand at room temperature for 24 hours, the light absorption spectra thereof were measured. Since HP-DTPA could not directly be conformed a competitive reaction system with NDA due to the UV absorption of itself, the decrease of the absorption of HP-DTPA at 368 nm was measured by using glucose or fructose as a standard substance in the same manner as above, after the reaction rate constants of glucose and fructose were determined using NDA. The decrease of absorbance of NDA or HP-DTPA was plotted according to Formula 8, and $k_X$ was calculated from slope of the regression line.

Figure 6:
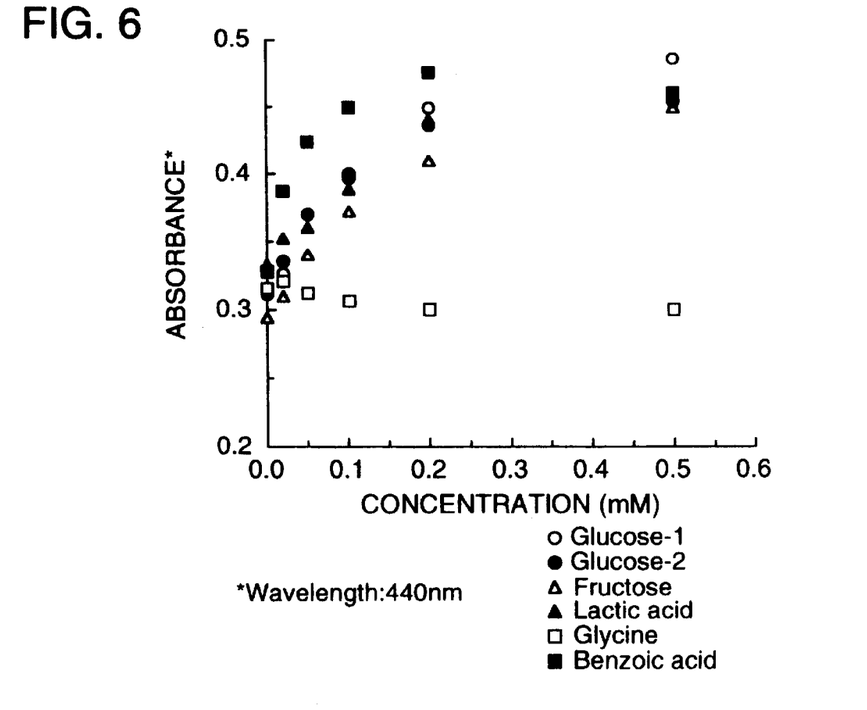
FIG. 6 is a graph illustrating how addition of a radiation-protecting agent brings about a decrease of light absorption of standard OH. scavenger, NDA (p-nitrosodimethylaniline).
Figure 7:
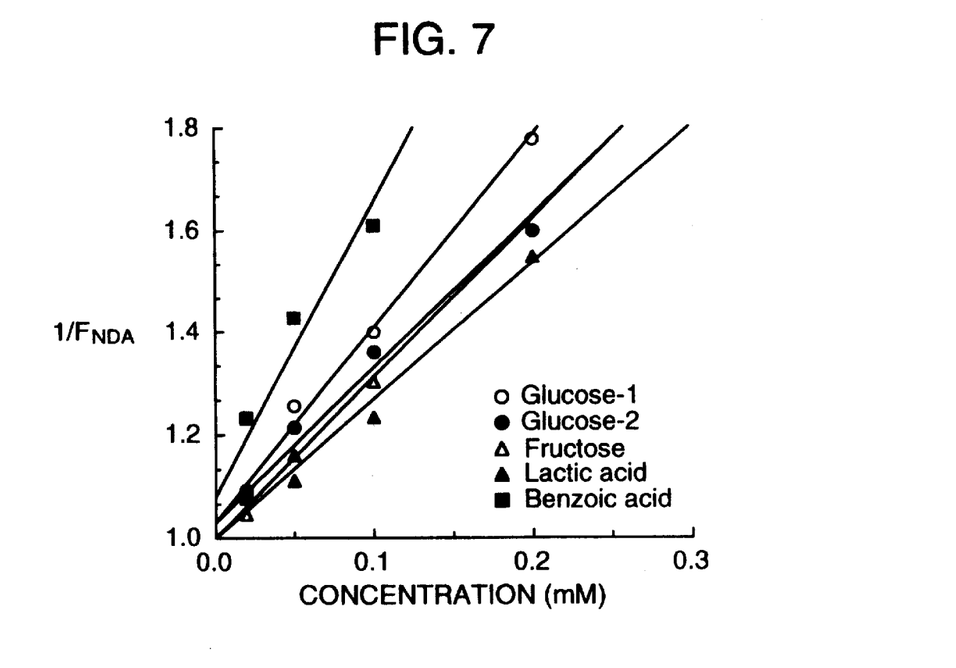
FIG. 7 is a graph given by plotting the decrease in light absorption of NDA (p-nitrosodimethylaniline) according to Equation 7.

In the experiments using NDA, the decrease of absorbance of NDA at 440 nm became smaller as the quantity of compound X increased, as seen in FIG. 6. This indicates that the OH. formed by the γ-ray of Tc-99m reacted with X. Plotting of $1/F_{NDA}$ according to Formula 7 gave a nearly linear relationship in the low concentration region (FIG. 7). The values of $k_X$ calculated from the slopes are shown in Table 1.

TABLE 1

Reaction rate constants with OH radical

| Compound | k ($M^{-1}s^{-1}$) |
|---|---|
| Glucose *) | $8.52 \times 10^8$ |
| Fructose | $6.77 \times 10^8$ |
| Lactic acid | $6.74 \times 10^8$ |
| Benzoic acid | $14.6 \times 10^8$ |
| HP-DTPA *) | $282.00 \times 10^8$ |

*) Reaction rate constants of glucose and HP-DTPA are average values of two measurements.

On the other hand, glycine did not inhibit the decrease of NDA absorbance, unlike the other compounds (FIG. 6). This is probably attributable to that a reaction between glycine and OH. formed glycine radical and the glycine radical further reacted with NDA, rather than that glycine did not react with OH.. Compounds with high reactivity are not suitable for use as a radiation-protecting agent, because such compounds may undergo further chain radical reaction and thereby eventually reacting with active ingredient. Amino acid is considered an example of such unsuitable compounds.

All the compounds tested herein were found to have a sufficiently high reaction rate constant, and considered useful as radiation-protecting agents except for amino acid.

EXAMPLE 3

A radiation-protecting agent was added to a radiopharmaceutical comprising a porphyrin derivative as an active ingredient. After labeling, whether the radiolysis of the active ingredient was actually inhibited by the radiation-protecting agent or not was examined.

Figure 8:
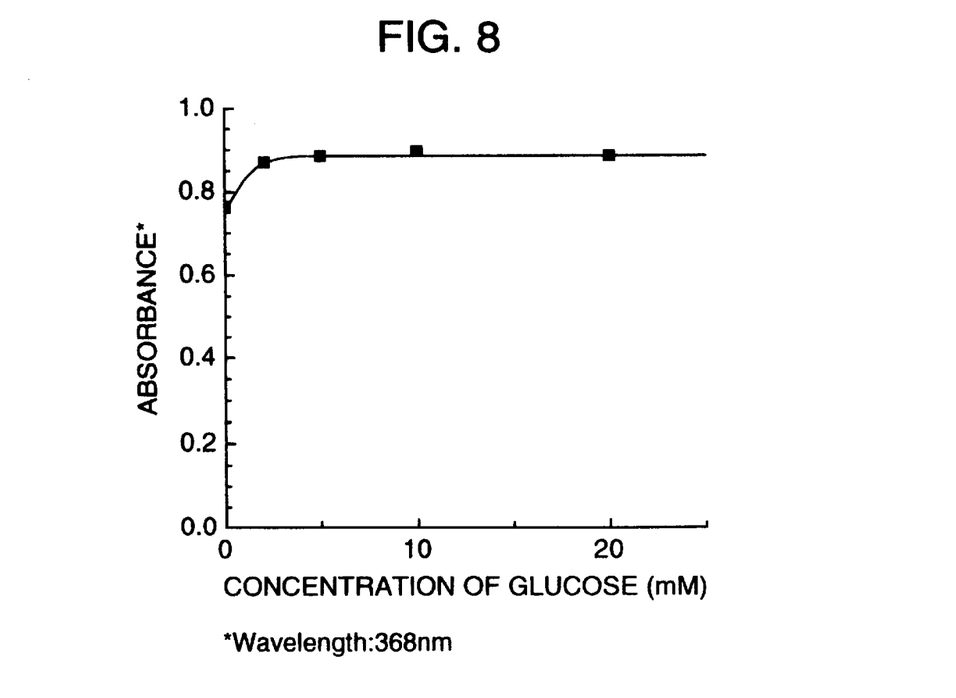
FIG. 8 is a graph demonstrating the fact that the radiolysis of HP-DTPA is inhibited by addition of a radiation-protecting agent, based on the change in UV absorption spectrum.

Various concentration (2.5, 5, 10 and 20 mM) of glucose was added to 0.2 mM solution of HP-DTPA formulated for use as a radiopharmaceutical. Then, 10 mCi of $^{99m}TcO_4^-$ was added, and the mixture thus obtained was allowed to stand at room temperature for 24 hours, after that UV absorption spectrum of each sample was measured. The results are shown in FIG. 8. The original HP-DTPA solution had a light absorbance of 0.88, which decreased to 0.76 when $^{99m}TcO_4^-$ was added. By adding glucose in an amount of 10 mM or more, the decrease in absorbance could be prevented completely. Since molar concentration of HP-DTPA was 0.2 mM, the radiolysis of HP-DTPA could completely be prevented when molar concentration of glucose was 50 times higher than that of HP-DTPA.

It was confirmed from the experimental result mentioned above that radiation-protecting agents of which reaction rate constant is around $10^8$ $M^{-1}s^{-1}$ can sufficiently exhibit the function thereof when molar quantity of such radiation-protecting agent present in the system is at least 50 times as high as molar quantity of active ingredient.

EXAMPLE 4

The radiation-protecting agent of the present invention is preferably unreactive with the active ingredient. In this experiment, whether or not a radiation-protecting agent reacts with active ingredient under an irradiated condition was examined.

Under the practical conditions for the manufacture of radiopharmaceuticals with porphyrin derivatives, eight samples shown in Table 2 were prepared. Each sample contained a HP-DTPA solution (10 mM), calcium chloride (12 mM), sodium chloride (80 mM), acetate buffer solution (pH 5.3, 20 mM), and $^{99m}TcO_4^-$ (100 mCi/ml) in addition to the ingredients shown in Table 2. After preparation, all the samples were allowed to stand in the dark at room temperature for 24 hours. Then, each sample was analyzed by reversed-phase HPLC for detecting the formation of fluorescent decomposition products in the HP-DTPA solution. The reversed-phase HPLC analysis was carried out an HPLC apparatus manufactured by Toso K. K. with a Puresil-C18 column (4.6 mm$\phi$×25 mmL) manufactured by Waters Co. As the eluent, a gradient system of 50 mM phosphate buffer (pH 3.5) and acetonitrile was used at a flow rate of 1 ml/minute, in which the concentration of acetonitrile was controlled so as to reach 15% in 0 minute, 30% in 15 minutes, 31% in 28 minutes, and 95% in 40–45 minutes. For detection, an UV detector (368 nm), a γ-ray detector and a fluorescence spectrometer (excitation: 378 nm; detection: 618 nm) were used. The results are shown in Table 2. It was demonstrated that the radiation-protecting agents other than ascorbic acid did not cause formation of fluorescent impurities and did not react with the active ingredient.

TABLE 2

Conditions of preparation and formation of fluorescent impurities

| Experiment # | Stabilizer* | [SnCl$_2$] ($\mu$g/ml) | Fluorescent impurities |
|---|---|---|---|
| 1 | — | — | Not detected |
| 2 | — | 200 | Not detected |
| 3 | Asc$^{a)}$ | — | Detected |
| 4 | Asc$^{a)}$ | 200 | Detected |
| 5 | Glu$^{b)}$ | 200 | Not detected |
| 6 | Suc$^{c)}$ | 200 | Not detected |
| 7 | Sol$^{d)}$ | 200 | Not detected |
| 8 | MEG$^{e)}$ | 200 | Not detected |

Note)
*Concentration of stabilizer is different from a run to another run.
$^{a)}$Asc: Ascorbic acid (2.5, 12.5, 25 mg/ml)
$^{b)}$Glu: Glucose (ca. 0.05, 0.5 M)
$^{c)}$Suc; Sucrose (ca. 0.05, 0.5 M)
$^{d)}$Sol: Sorbitol (ca. 0.05, 0.5 M)
$^{e)}$MEG: Meglumin (ca. 0.05, 0.5 M)

In the test using ascorbic acid as a stabilizer, fluorescent impurities were formed. This result indicates that the use of ascorbic acid may not be appropriate when the active ingredient has a high reactivity. It can be concluded from these results that the radiation-protecting agents of the present invention can exhibit a high usefulness even in cases where ascorbic acid which is a conventional stabilizer frequently used hitherto cannot be used.

What is claimed is:

1. A radiopharmaceutical containing a reducible radiolabeled active ingredient and a radiation-protecting agent which comprises an organic compound having high physiological acceptability and being usable in medical drugs and having reactivity with water radicals selected from the group consisting of a OH radical, a H radical and a hydrated electron in a range of from $1\times10^8$ M$^{-1}$s$^{-1}$ to $5\times10^{10}$ M$^{-1}$s$^{-1}$, wherein said compound protects said reducible radiolabeled active ingredient in the radiopharmaceutical against the action of radiation.

2. A radiopharmaceutical according to claim 1, wherein said organic compound having high physiological acceptability is not reactive with said reducible radiolabeled active ingredient in the radiopharmaceutical.

3. A radiopharmaceutical according to claim 1, wherein said organic compound having high physiological acceptability is a monosaccharide, or a disaccharide, or an organic acid or a salt thereof or an ester thereof.

4. A radiopharmaceutical according to claim 1, wherein said organic compound having high physiological acceptability comprises at least one member selected from the group consisting of glucose, fructose, mannose, galactose, sucrose, maltose, lactose, arabinose, sorbitol, meglumin, sialic acid, lactic acid and benzoic acid or a salt thereof or an ester thereof.

5. A radiodiagnostic agent which contains a radiopharmaceutical according to claims 1, 2, 3 or 4, providing that molar concentration of the radiation-protecting agent is at least 50 times as high as the molar concentration of the active ingredient.

6. A radiotherapeutic agent which contains a radiopharmaceutical according to claims 1, 2, 3 or 4, provided that molar concentration of the radiation-protecting agent is at least 50 times as high as the molar concentration of the active ingredient.

7. A radiodiagnostic agent according to claim 5, wherein said radioisotope is any one member selected from the group consisting of Tc-99m, I-123, I-131, Ga-67, In-111, C-11, N-13, O-15, F-18, Ga-68, Cu-62 and Rb-87.

8. A radiotherapeutic agent according to claim 6, wherein said radioisotope is any one member selected from the group consisting of Y-90, I-131, Sm-153, Dy-165, Ho-166, Lu-177, Re-186, Re-188, At-211 and Cu-67.

9. A method of protecting a reducible radiolabeled active ingredient in a radiodiagnostic agent or a radiotherapeutic agent with a radiation-protecting agent comprising: radiolabeling the active ingredient of the radiodiagnostic agent with a radioisotope selected from the group consisting of Tc-99m, I-123, I-131, Ga-67, In-111, C-11, N-13, O-15, F-18, Ga-68, Cu-62 and Rb-87, or radiolabeling the active ingredient of the radiotherapeutic agent with a radioisotope selected from the group consisting of Y-90, I-131, Sm-153, Dy-165, Ho-166, Lu-177, Re-186, Re-188, At-211 and Cu-67, and adding to the radiodiagnostic agent or radiotherapeutic agent a radiation-protecting agent to protect said reducible radiolabeled active ingredient against the action of radiation, said radiation protecting agent comprising an organic compound reacting with water radicals, selected from the group consisting of a OH radical, a H radical and a hydrated electron in a range of from $1\times10^8$ M$^{-1}$s$^{-1}$ to $5\times10^{10}$ M$^{-1}$s$^{-1}$ wherein the molar concentration of said radiation-protecting agent is at least 50 times as high as the molar concentration of the active ingredient of said radiodiagnostic agent or radiotherapeutic agent.

* * * * *

UNITED STATES PATENT AND TRADEMARK OFFICE
CERTIFICATE OF CORRECTION

PATENT NO. : 6,027,710
DATED : February 22, 2000
INVENTOR(S) : Kazuo HIGASHI, Komei WASHINO

It is certified that error appears in the above-indentified patent and that said Letters Patent is hereby corrected as shown below:

ON THE TITLE PAGE
Item

[73] Assignee change "Nihon Medi-Physiscs Co., Ltd." to --Nihon Medi-Physics Co., Ltd.--

Signed and Sealed this

Twenty-seventh Day of March, 2001

Attest:

NICHOLAS P. GODICI

Attesting Officer

Acting Director of the United States Patent and Trademark Office